US00PP27924P3

(12) United States Plant Patent
Kordes

(10) Patent No.: US PP27,924 P3
(45) Date of Patent: Apr. 25, 2017

(54) SHRUB ROSE PLANT NAMED 'KORMAHENSI'

(50) Latin Name: *Rosa hybrida*
Varietal Denomination: KORmahensi

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 48 days.

(21) Appl. No.: 14/756,367

(22) Filed: Sep. 2, 2015

(65) Prior Publication Data

US 2017/0064886 P1 Mar. 2, 2017

(51) Int. Cl.
*A01H 5/02* (2006.01)

(52) U.S. Cl.
USPC ..... Plt./107

(58) Field of Classification Search
USPC ..... Plt./107
See application file for complete search history.

*Primary Examiner* — Keith Robinson

(57) ABSTRACT

'KORmahensi' is a new and distinct variety of *Rosa hybrida* which is characterized by the combination of an upright and bushy growth habit and large, very-double flowers which are pink in color. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORmahensi'.

BACKGROUND OF THE INVENTION

The present invention relates to a new and distinct *Rosa hybrida*, shrub rose cultivar, which has been given the variety denomination of 'KORmahensi'. Its market class is PLT/102.

Parentage: The *Rosa hybrida* variety 'KORmahensi' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORmahensi' from all other varieties known to the inventor.

'KORmahensi' is a seedling selection which resulted from the controlled pollination of *Rosa hybrida* 'AUSham' (U.S. Plant Pat. No. 11,421), the seed parent, and an unnamed breeding line developed and owned by the same inventor, the pollen parent, during the summer of 2003.

As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2004 from the seedling beds due to its superior characteristics and asexually propagated for further evaluation. This new and distinctive rose variety was given the name 'KORmahensi'.

Asexual Reproduction: The first asexual propagation of 'KORmahensi' was performed in July of 2004 at the inventor's nursery in Offenseth-Sparrieshoop, Germany. Subsequently, 'KORmahensi' has been successfully propagated by stem cuttings and grafting in Jackson County, Oreg. These initial and other subsequent propagations conducted in controlled environments demonstrate that 'KORmahensi' reproduces true to type in successive generations of asexual reproduction.

SUMMARY OF THE INVENTION

The following characteristics have been repeatedly observed and represent the distinguishing characteristics of the new *Rosa hybrida* cultivar 'KORmahensi'. These traits, in combination, distinguish 'KORmahensi' as a new and distinct cultivar.

1. *Rosa hybrida* 'KORmahensi' exhibits an upright, bushy growth habit; and
2. *Rosa hybrida* 'KORmahensi' exhibits an abundance of flowers; and
3. *Rosa hybrida* 'KORmahensi' exhibits a double flower habit; and
4. *Rosa hybrida* 'KORmahensi' exhibits a large flower size; and
5. *Rosa hybrida* 'KORmahensi' exhibits a pink flower color, at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORmahensi', taken from plants of one and a half years of age.

DETAILED BOTANICAL DESCRIPTION

The following is a detailed botanical description of a new and distinct variety of *Rosa hybrida* known as 'KORmahensi', based upon field observations made in June of 2015 from one and a half year old plants, grown in-ground, at a nursery in Jackson County, Oreg.

Those skilled in the art will appreciate that certain characteristics will vary with older or, conversely, with younger plants. 'KORmahensi' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORmahensi' and comparisons with other varieties of *Rosa hybrida* are provided below.

General plant description:

*Growth rate*.—Vigorous.

*Growth habit*.—Upright to bushy.

*Mature dimensions*.—Approximately 130 cm tall and 60 cm wide.

*Cold hardiness*.—USDA Hardiness Zones 5 to 9.

*Propagation*.—Grafting and stem cuttings.

*Disease resistance*.—Excellent resistance to powdery mildew (*Sphaerotheca pannosa*), blackspot (*Diplocarpon rosae*) and rust (*Phragmidium* sp.) diseases under normal growing conditions in Jackson County, Oreg.

Root system: Fibrous.

Stems:

*Stem color*.—Immature stems are Yellow-Green Group 144B; mature stems are Yellow-Green Group 144A.

*Anthocyanin intonations*.—Greyed-Red Group 178B present on immature wood.

*Stem surface texture*.—Immature stems exhibit a smooth texture while mature stems exhibit a rough texture.

*Stem dimensions*.—Typical mature stems are approximately 60 cm long and 8 mm in diameter near the base.

*Prickles*.—Incidence — Present on mature stems only; 20 prickles per 10 cm of stem, on average. Size — Average length is 1 to 6 mm. Immature prickle color — Yellow-Green Group 145A. Mature prickle color — Yellow-Green Group 145A, senescing to Greyed-Orange Group 166D. Anthocyanin intonations — Greyed-Red Group 178A present on immature prickles only. Shape — Deeply concave. Texture — Smooth.

Leaves:

*Arrangement*.—Imparipinnate compound leaves; mature axillary leaves consisting of 5 leaflets.

*Attachment*.—Petiolate.

*Dimensions*.—165 mm long and 115 mm wide, on average.

*Abundance*.—Abundant.

*Stipules*.—Size — 25 mm long and 8 mm wide. Stipule color — Yellow-Green Group 144A. Anthocyanin intonations — Greyed-Red Group 179B; present on the adaxial surface of the midrib. Stipitate glands — Limited; only present at margins. Margins — Glandular toothed. Texture, adaxial surface — Smooth. Texture, abaxial surface — Smooth. Apex — Apiculate. Base — Winged.

*Petiole*.—Length — Average 45 to 55 mm. Diameter — Average 2 to 3 mm. Petiole color, adaxial surface — Yellow-Green Group 144A. Petiole color, abaxial surface — Yellow-Green Group 144A. Margins — Glandular toothed. Anthocyanin intonations — Greyed-Red Group 178A; present on prickles, stipitate glands and the adaxial surface of the midrib. Prickles — A few small prickles on the abaxial surface. Stipitate glands — Limited number present on margins and abaxial surface. Texture — Hispid. Strength — Strong.

*Rachis*.—Length — Average 20 to 30 mm. Diameter — Average 1 to 2 mm. Color — Yellow-Green Group 144A. Anthocyanin intonations — Greyed-Red Group 179B; present on prickles, stipitate glands and the adaxial surface of the midrib. Margins — Glandular toothed. Texture — Hispid. Prickles — A few small prickles underneath. Stipitate glands — Limited number present on margins and abaxial surface.

*Leaflets*.—Quantity — Normally 5 leaflets on normal leaves in middle of the stem. Dimensions — Average size of the terminal leaflet is 55 to 60 mm long and 45 to 50 mm wide. Shape — Elliptical. Apex — Cuspidate. Base — Obtuse. Margins — Serrated. Texture, adaxial surface — Glossy and smooth. Texture, abaxial surface — Matte and leathery. Juvenile foliage color, adaxial surface — Yellow-Green Group 146B. Juvenile foliage color, abaxial surface — Yellow-Green Group 146C. Mature foliage color, adaxial surface — Yellow-Green Group 147A. Mature foliage color, abaxial surface — Yellow-Green Group 148B. Anthocyanin intonations — Greyed-Orange Group 176A. Present at margins, abaxial surfaces, petiole, rachis and petiolule of juvenile foliage. Venation — Reticulate. Petiolule — Dimensions — 3 mm long and 1 to 2 mm in diameter. Petiolule color, adaxial and abaxial surfaces — Yellow-Green Group 144C. Anthocyanin intonations — Greyed-Red Group 179C present on the adaxial surface. Prickles — None present. Stipitate Glands — Present along margins and on the abaxial surface. Texture, adaxial and abaxial surfaces — Papillate with a few fine hairs present.

Inflorescence:

*Inflorescence type*.—Both panicles with multiple flowers and solitary flowers observed.

*Blooming habit*.—Recurrent.

*Quantity of flowers*.—Generally 1 to 4 flowers on panicles.

*Size*.—Panicles are 150 mm tall and 130 mm wide, on average.

*Peduncle*.—Surface — Glabrous. Length — 30 to 50 mm average length. Diameter — 3 to 6 mm average diameter. Color — Yellow-Green Group 144A.

Anthocyanin intonations — Greyed-Purple Group 184A. Strength — Strong. Texture — Smooth.

Flowering laterals: Present below the initiation of inflorescence. Generally 1 to 3 flowering laterals are present, with 3 to 8 flowers per flowering shoot.

Bud:

*Bud form*.—Short; globular.

*Size*.—Upon opening, 35 mm in length from base of receptacle to distal end of bud and 30 mm diameter at its widest point.

*Texture*.—Leathery.

*Color, as sepals first unfold*.—Red-Purple Group 58B.

*Color when one-quarter open, upper surface*.—Marginal zone — Red Group 52B. Middle zone — Red Group 52B. Basal zone — Orange Group 29B. Basal spot — Yellow Group 4A.

*Color when one-quarter open, lower surface*.—Marginal zone — Red-Purple Group 58B. Middle zone — Red-Purple Group 58C. Basal zone — Red Group 48B. Basal spot — Yellow Group 4A.

Flower:

*Pedicel*.—Surface — Lightly pubescent with a limited number of fine hairs. Length — 60 to 70 mm, on average. Diameter — 3 to 4 mm, on average. Color — Yellow-Green Group 144B. Anthocyanin intonations — Greyed-Red Group 182A. Strength — Somewhat strong. Texture — Smooth.

*Sepals*.—Diameter of calyx — 20 to 30 mm, at anthesis. Color, adaxial surface — Greyed-Green Group 194A. Color, abaxial surface — Yellow-Green Group 144B. Anthocyanin intonations — Greyed-Red 182A. Size — 20 to 25 mm long and 10 mm wide, on average. Apex — Apiculate. Base — Flat at union with receptacle. Quantity — Five. Texture, adaxial surface — Hoary. Texture, abaxial surface — Leathery. Margins — Cilliate. Stipitate glands — Limited; along margins.

*Corolla*.—General shape of corolla — Rosette. Shape of corolla when viewed from the side — Upon opening, upper portion — Flat. Upon opening, lower portion — Concave. Open flower, upper portion — Flattened convex. Open flower, lower portion — Concave. Aspect — Flowers held upright.

*Dimensions*.—Large for a shrub rose. When open, the average flower diameter is 85 to 95 mm and the average flower height is 50 mm.

*Fragrance*.—Strong.

*Duration*.—On the plant 5 days. Senesced petals drop away cleanly.

*Petals*.—Petal arrangement — Not formal. Petal count — Exhibits very-double flowers with approximately 45 to 50 petals under normal conditions. Petal reflex — Outermost petals are slightly reflexed. Petal reflex occurs one by one. Petal margin — Entire, with some of the innermost petal margins being ruffled. Petal shape — Obovate. Apex — Obtuse; emarginate. Base — Cuneate. Dimensions — Approximately 30 to 50 mm long and 25 to 50 mm wide. Texture, inner surface — Smooth. Texture, outer surface — Smooth. Petal color, upon opening — Outermost petals, outer surface — Marginal zone — Red-Purple Group N66C. Middle zone — Red-Purple Group 62A. Basal zone — Red Group 37B. Outermost petals, inner surface — Marginal zone — Red-Purple Group 58B. Middle zone — Red-Purple Group 63C with intonations of Red Group 37B. Basal zone — Red Group 37B. Innermost petals, outer surface — Red-Purple Group N66C with intonations of Yellow Group 4B along the midrib. Innermost petals, inner surface — Marginal zone — Red-Purple Group 62A. Middle zone — Red-Purple Group 62A. Basal zone — Red Group 38B. Basal petal spots, upon opening — Basal petal spot, outermost petals — Dimensions — 5 to 7 mm high and 7 mm wide. Color, outer surface — Yellow Group 4B. Color, inner surface — Yellow Group 5A. Basal petal spot, innermost petals — Dimensions — 5 mm high and 5 mm wide. Outer surface — Yellow Group 4B. Inner surface — Yellow Group 4A. Petal color, after opening — Outermost petals, outer and inner surfaces — Marginal zone — Red-Purple Group 58C. Middle zone — Red-Purple Group 62C. Basal zone — Red-Purple Group 62D. Innermost petals, outer surface — Marginal zone — Red-Purple Group 63C. Middle zone — Red-Purple Group 62C. Basal zone — Red-Purple Group 62D. Innermost petals, inner surface — Marginal zone — Red-Purple Group 63C. Middle zone — Red-Purple Group 63D. Basal zone — White Group N155C with occasional intonations of Yellow Group 6A. Basal petal spots, after opening — Basal petal spot, outermost petals — Dimensions — 5 mm high and 3 mm wide. Color, outer surface — A combination of Yellow Group 4B and 4C. Color, inner surface — A combination of Yellow Group 4A and 4B. Basal petal spot, innermost petals — Dimensions — 3 mm high and 2 mm wide. Outer surface — Yellow Group 6B. Inner surface — Yellow Group 6A. General Tonality — Red-Purple Group 58C, at anthesis, and fading to Red-Purple Group 65B after 3 days.

*Petaloids*.—Quantity — 5 to 10 petaloids per flower, on average. Dimensions — Approximately 20 to 30 mm long and 10 to 25 mm wide. Color, inner and outer surfaces — A combination of Red Group 63B, 63C, and 63D. Intonations of Yellow Group 4D are present in the basal zone and along the midrib. Margins — Undulated. Shape — Spatulate; highly irregular. Apex — Acute. Base — Attenuate. Texture, inner and outer surfaces — Smooth.

Reproductive organs:

*Stamens*.—Quantity — Approximately 130, on average, and regularly arranged around the styles. Anthers — Dimensions — 1.5 to 2 mm long and 1 mm wide, on average. Color — Greyed-Orange Group 163A. Pollen — Generally present; medium density. Pollen Color — Greyed-Orange Group 163A. Filaments — Color — Yellow Group 8A. Length — 10 to 15 mm.

*Pistils*.—Quantity — Average; approximately 65 present. Stigmas — Dimensions — 1 mm long and 1 mm wide. Location — Inferior to anthers. Color — Yellow-Orange Group 16B. Styles — Length — Approximately 5 to 7 mm long. Color — Red Group 49A.

*Ovary*.—Dimensions — 3 mm long and 1 mm in diameter. Color — Greyed-Green Group 193D.

*Receptacle*.—Shape — Urn-shaped. Dimensions — Approximately 8 to 9 mm high and 12 to 13 mm wide. Surface — Glabrous and slightly glaucous.

Color — Yellow-Green Group 144B with intonations of Greyed-Purple Group 183C. Texture — Smooth.

Hips and seed formation: Not observed.

Comparisons with the parents:

*The new rose plant may be distinguished from its seed parent, Rosa hybrida 'AUSham', by the following combination of characteristics.*—1. 'KORmahensi' exhibits a pink flower color, whereas 'AUSham' exhibits a light-pink flower color. 2. 'KORmahensi' exhibits strong fragrance, whereas 'AUSham' exhibits light fragrance.

*The new rose plant may be distinguished from its pollen parent, an unnamed seedling, by the following combination of characteristics.*—1. 'KORmahensi' exhibits a large flower size, whereas the pollen parent exhibits a medium flower size. 2. 'KORmahensi' exhibits very-double flowers, whereas the pollen parent exhibits semi-double flowers. 3. 'KORmahensi' exhibits an upright and bushy growth habit, whereas the pollen parent exhibits a compact growth habit.

Comparisons with similar *Rosa hybrida* cultivars known to the inventor: For a comparison, several physical characteristics of the rose variety 'KORvioros', a rose variety from the same inventor described and illustrated in U.S. Plant patent application Ser. No. 13/998,343 are compared to 'KORmahensi' in Chart 1.

CHART 1

| Characteristic | 'KORmahensi' | 'KORvioros' |
|---|---|---|
| Bud color as sepals first unfold. | Red-Purple Group 58B. | Yellow-Orange Group 23B. |
| General tonality of flower, at anthesis. | Red-Purple Group 58C. | Yellow Group 10B. |
| Incidence of prickles. | 20 per 10 cm of stem. | 60 to 80 per 10 cm of stem. |

That which is claimed:

1. A new and distinct variety of rose plant named 'KORmahensi', as described and illustrated herein.

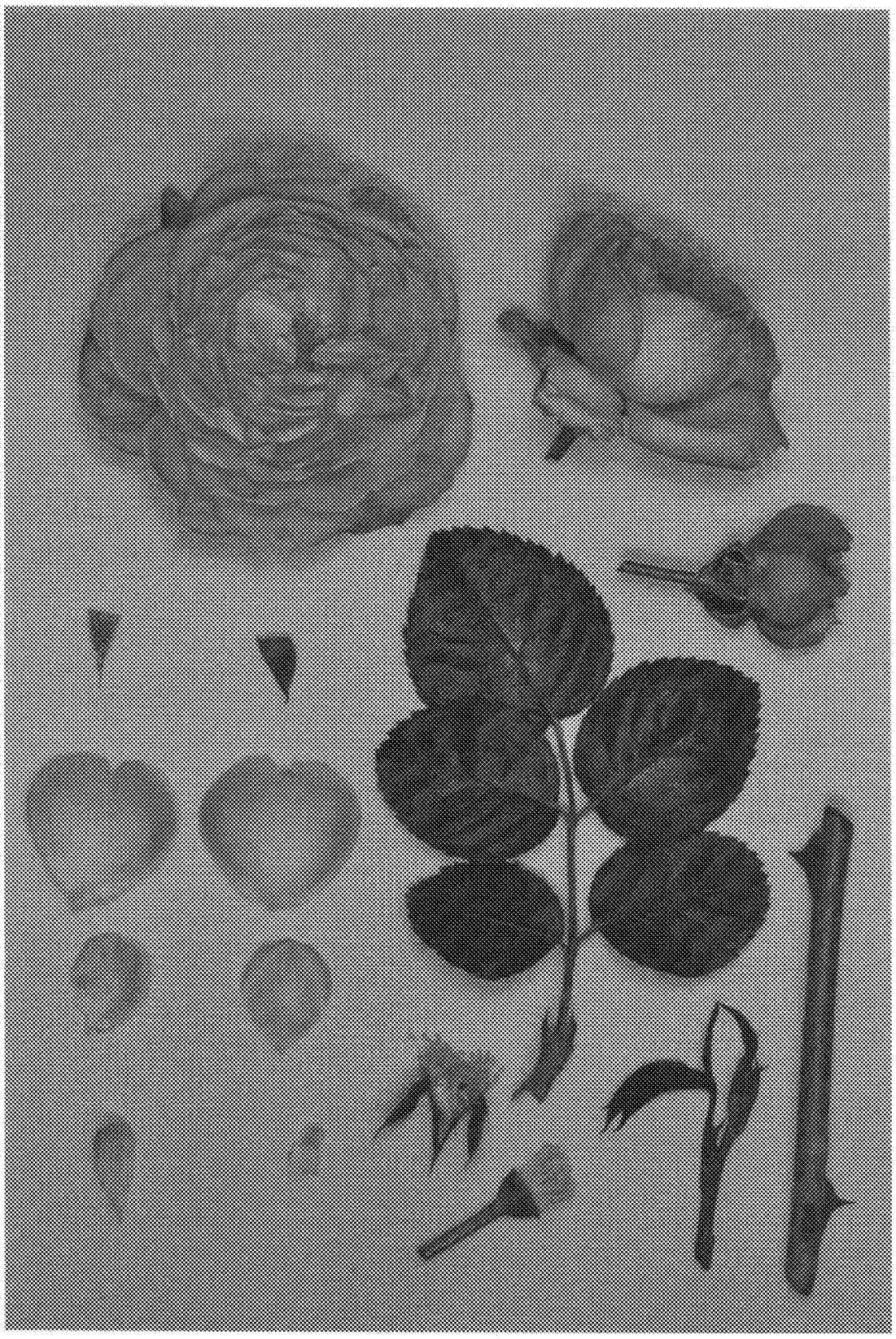

* * * * *